United States Patent
Wu et al.

(10) Patent No.: US 7,542,142 B2
(45) Date of Patent: *Jun. 2, 2009

(54) OPTICAL PROBES AND PROBE SYSTEMS FOR MONITORING FLUID FLOW IN A WELL

(75) Inventors: Xu Wu, Beijing (CN); Elizabeth B. Dussan V, Ridgefield, CT (US); Oliver C. Mullins, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 62 days.

This patent is subject to a terminal disclaimer.

(21) Appl. No.: 11/457,642

(22) Filed: Jul. 14, 2006

(65) Prior Publication Data
US 2006/0242853 A1 Nov. 2, 2006

Related U.S. Application Data

(62) Division of application No. 10/055,420, filed on Jan. 23, 2002, now Pat. No. 7,142,306.

(60) Provisional application No. 60/263,531, filed on Jan. 23, 2001.

(51) Int. Cl.
*G01N 21/00* (2006.01)
*G01N 21/55* (2006.01)
*G01N 15/06* (2006.01)
*G01N 21/49* (2006.01)
*G01N 21/85* (2006.01)
*G01V 5/00* (2006.01)
*G01V 5/04* (2006.01)
*G02B 6/00* (2006.01)
*G02B 6/26* (2006.01)
*G02B 6/42* (2006.01)

(52) U.S. Cl. ............... 356/436; 356/445; 250/256; 250/573; 385/12; 385/31

(58) Field of Classification Search ............... None
See application file for complete search history.

(56) References Cited

U.S. PATENT DOCUMENTS 2,334,475 A 11/1943 Claudet
3,315,160 A 4/1967 Goodman (Continued)

OTHER PUBLICATIONS

Xu Wu et al., "Using an optical sensor to quantify the amount of oil, water and gas in a water-continuous flow," SPIE Proceedings: Internal Standardization and Calibration Architectures of Chemical Sensors vol. 3856. Eds. Ronald E. Shaffer and Radislav A. Potyrailo (1999): pp. 298-307.

(Continued)

*Primary Examiner*—Gregory J Toatley, Jr.
*Assistant Examiner*—Gordon J Stock, Jr.
(74) *Attorney, Agent, or Firm*—David Gordon; Vincent Loccisano; Jody DeStefanis

(57) ABSTRACT

Several optical probes useful in downhole applications are provided. A first probe has a tip in the form of a cubical corner with the diagonal of the cubical corner aligned with the axis of the probe. A second probe has a tip formed in a 45° cone. In these designs, light will bounce respectively three times or twice, but still retain the same orientation. To facilitate drainage, the very tip of the probe may be rounded. Both designs also provide a probe with a large numerical aperture and both are useful for detecting reflectance and the holdup of a multiphase fluid. A third probe uses (hemi)spherical or paraboloid probe tip. The third probe tip has a small numerical aperture and is useful for detecting fluorescence and oil velocity. In all three embodiments, the base behind the probe tip may be tapered to facilitate fluid drainage.

10 Claims, 4 Drawing Sheets

U.S. PATENT DOCUMENTS

| | | | |
|---|---|---|---|
| 3,586,895 A * | 6/1971 | Sowers et al. | 313/524 |
| 3,945,371 A | 3/1976 | Adelman | |
| 4,197,458 A * | 4/1980 | Perren | 250/341.2 |
| 4,287,427 A * | 9/1981 | Scifres | 250/577 |
| 4,500,204 A | 2/1985 | Ogura | |
| 4,542,987 A | 9/1985 | Hirschfeld | |
| 4,625,724 A | 12/1986 | Suzuki et al. | |
| 4,626,110 A | 12/1986 | Wickersheim et al. | |
| 4,659,218 A * | 4/1987 | de Lasa et al. | 356/133 |
| 4,693,244 A * | 9/1987 | Daikuzono | 606/16 |
| 4,979,797 A * | 12/1990 | Nemeth | 73/293 |
| 5,029,471 A * | 7/1991 | Goodrich | 73/293 |
| 5,044,723 A | 9/1991 | MacDonald | |
| 5,074,632 A | 12/1991 | Potter | |
| 5,363,458 A | 11/1994 | Pan et al. | |
| 5,364,186 A | 11/1994 | Wang et al. | |
| 5,371,826 A | 12/1994 | Friedman | |
| 5,430,813 A | 7/1995 | Anderson et al. | |
| 5,517,024 A | 5/1996 | Mullins et al. | |
| 5,526,112 A | 6/1996 | Sahagen | |
| 5,598,493 A | 1/1997 | Bonham et al. | |
| 5,604,582 A | 2/1997 | Rhoads et al. | |
| 5,664,036 A | 9/1997 | Islam | |
| 5,812,729 A | 9/1998 | Allison et al. | |
| 5,831,743 A | 11/1998 | Ramos et al. | |
| 5,901,261 A * | 5/1999 | Wach | 385/38 |
| 5,918,190 A | 6/1999 | Nadeau | |
| 5,956,132 A | 9/1999 | Donzier | |
| 6,016,191 A | 1/2000 | Ramos et al. | |
| 6,023,340 A | 2/2000 | Wu et al. | |
| 6,075,611 A | 6/2000 | Dussan V. et al. | |
| 6,124,597 A | 9/2000 | Shehada et al. | |
| 6,236,783 B1 | 5/2001 | Mononobe et al. | |
| 6,246,817 B1 | 6/2001 | Griffin | |
| 6,263,133 B1 | 7/2001 | Hamm | |
| 6,416,234 B1 | 7/2002 | Wach et al. | |
| 6,472,205 B1 | 10/2002 | Tsien et al. | |
| 6,704,109 B2 | 3/2004 | Wu et al. | |
| 6,850,317 B2 | 2/2005 | Mullins et al. | |
| 7,142,306 B2 * | 11/2006 | Wu et al. | 356/436 |

OTHER PUBLICATIONS

Wang, Xin and Oliver C. Mullins, Fluorescence Lifetime Studies of Crude Oils, Applied Spectroscopy, vol. 48, No. 8 (1994): pp. 977-984.

Groenzin et al., "Resonant Fluorescence Quenching of Aromatic Hydrocarbons by Carbon Dusulfide." J. Phys. Chem. A. 103 (1999): 1504-1508.

Zhu et al., "Temperature Dependence of Fluorescence of Crude Oils and Related Compounds." Energy and Fuels 6 (1992): pp. 545-552.

Ralston et al. "Quantum Yields of Crude Oils." Applied Spectroscopy vol. 59, No. 12 (1996): pp. 1563-1568.

Mannoh et al., "High Power and high-temperature operation of GaInP/AIGaInP strained multiple quantum well lasers", Appl. Phys. Lett. 62, 1173-1175, Mar. 15, 1993.

\* cited by examiner

OPTICAL PROBES AND PROBE SYSTEMS FOR MONITORING FLUID FLOW IN A WELL

This application is a divisional of and claims priority from U.S. Ser. No. 10/055,420, filed Jan. 23, 2002 now issued as U.S. Pat. No. 7,142,306, which claims the benefit of provisional patent application Ser. No. 60/263,531 filed Jan. 23, 2001, both of which are hereby incorporated by reference herein in their entireties.

This application is related to co-owned U.S. Pat. No. 5,831,743 entitled "Optical Probes", U.S. Pat. No. 5,956,132 entitled "Method and Apparatus for Optically Discriminating Between the Phases of a Three-Phase Fluid", U.S. Pat. No. 6,016,191 entitled "Apparatus and Tool Using Tracers and Single Point Optical Probes for Measuring Characteristics of Fluid Flow in a Hydrocarbon Well and Methods of Processing Resulting Signals", U.S. Pat. No. 6,023,340 entitled "Single Point Optical Probe for Measuring Three-Phase Characteristics of Fluid Flow in a Hydrocarbon Well", and U.S. Pat. No. 6,075,611 entitled "Methods and Apparatus Utilizing a Derivative of a Fluorescence Signal for Measuring the Characteristics of a Multiphase Fluid Flow in a Hydrocarbon Well", all of which are hereby incorporated by reference herein in their entireties.

This application is also related to co-owned, U.S. Ser. No. 10/055,070 entitled "Apparatus and Methods for Determining Velocity of Oil in a Flow Stream" and U.S. Ser. No. 10/055,654 (now issued as U.S. Pat. No. 6,704,109) entitled "Downhole Fluorescence Detection Apparatus" both of which are hereby incorporated by reference herein in their entireties.

BACKGROUND OF THE INVENTION

1. Field of the Invention

The present invention relates to oil well optical apparatus. The present invention more particularly relates to fiber optical probes which are suitable for investigating fluid flow in a well.

2. State of the Art

The use of optical systems for the analysis of fluids is well known. For example, as set forth in the patents incorporated by reference above, optical probes can be used downhole for measuring oil, water, and gas holdup in three-phase flows. In particular, light of excitation is coupled to a small optical probe that is deployed into a sample flow. Depending on the optical properties of the fluid surrounding the probe, the returning signal carries the optical signature of the fluid. Gas will induce a large reflectance, compared with liquids, due to the large mismatch of the index of refraction. Crude oils, on the other hand, will produce fluorescence under illumination. By analyzing both the reflectance and the fluorescence signals, the nature of the fluid in contact with the probe can be identified.

As noted in the previously incorporated patents, using a flat tip probe (normal incidence), the contrast between the indices of refraction for water and oils is much more subtle than the contrast between the indices of refraction for gas and liquid. To enhance the contrast, off-normal incidence was proposed such as the 45 and 60 oblique tip designs and the 5/50 biconical tip design. While the previously incorporated patents represent a major step forward in downhole analysis of fluids, the probes described therein are not necessarily optimal in certain circumstances.

SUMMARY OF THE INVENTION

It is therefore an object of the invention to provide optical probes which are suitable for investigating the flow of fluids in a well.

It is another object of the invention to provide optical probe tip designs which are optimized for the measurement principle which with the probe is to be utilized.

It is a further object of the invention to provide optical probe tip designs which minimize interference with the fluid flow.

In accord with the objects of the invention, a first probe of the invention is particularly designed for sensing reflectance and has a tip which comprises a cubical corner; i.e., three planes perpendicular to each other, where the diagonal of the cubical corner aligns with the axis of the probe. Light coming towards such a probe tip will be subjected to triple partial reflections (once at each surface) and be sent back. For rays that are parallel to the probe axis, the incident angle at each of the three planes is the same and equals 54.73 degrees.

A second probe of the invention is also designed for sensing reflectance and has a tip formed in a 45 cone. In this design, the light will bounce twice (instead of three times in the cubical corner design), but still retain the same orientation. In order to facilitate drainage of fluids about the probe tip (e.g., to reduce residue films), the second probe tip (and the first probe tip) may be rounded off. In addition, if desired, the base behind the tip may be tapered.

A third probe of the invention is designed for sensing fluorescence and comprises a probe tip which is spherical or parabolic. A spherical tip facilitates fluid drainage. In addition, with a spherical or nearly spherical tip, the numerical aperture (NA) of the probe is reduced and a pencil-like beam that reaches a relatively long distance from the tip is generated. The beam is effectively far-sighted and is particularly useful for the determination of oil velocity.

Additional objects and advantages of the invention will become apparent to those skilled in the art upon reference to the detailed description taken in conjunction with the provided figures.

BRIEF DESCRIPTION OF THE DRAWINGS

FIG. 2b is an end view of the cubical corner probe tip of FIG. 2a;

DETAILED DESCRIPTION OF THE PREFERRED EMBODIMENTS

For purposes of illustration, the invention will be described primarily with reference to a production logging tool. However, at the outset, it should be appreciated by those skilled in the art that the invention can be implemented in conjunction with many different types of tools. In addition, it will be appreciated by those skilled in the art that the invention can be implemented as a permanent installation in a producing well.

Figure 1:
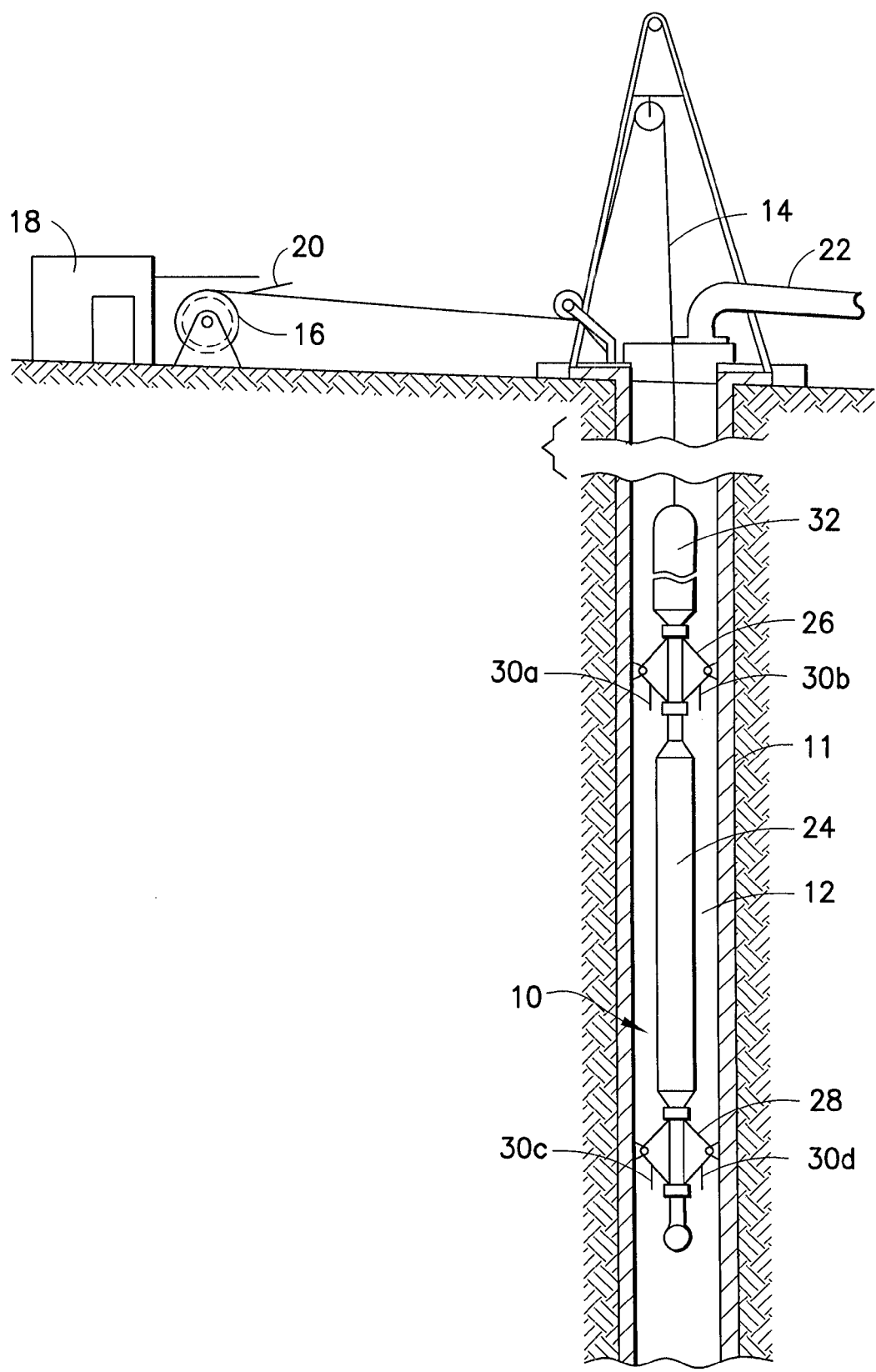
FIG. 1 is a schematic diagram of a production logging tool incorporating the probes of the invention and coupled to associated surface equipment.

Referring now to FIG. 1, a production logging tool 10 is suspended in a well 12 by means of a cable 14 which is coupled to a winch 16 for raising and lowering the tool 10. The cable 14 includes conductors (not shown) which may be either electrical or optical, or both, for communicating with data processing equipment 18 located on the surface. A cable displacement detector 20 is also provided at the surface in order to determine the depth of the tool 10 when it is lowered into the well 12. During production, fluid from the well is collected at the surface and conducted by a duct 22 to a storage or refining facility (not shown).

The tool 10 may take any of various forms such as disclosed in previously incorporated U.S. patents, or the previously incorporated concurrently filed applications. As shown in FIG. 1, the tool generally includes an elongate body 24 which is centered (or otherwise oriented) in the casing 11 of the well 12 by upper and lower bow springs 26, 28 (although only one set of bow springs is required for centering). The tool 10 is provided with a plurality of optical probes, e.g. 30a, 30b, 30c, 30d, which are located in the casing by the springs 26, 28. According to one embodiment of the invention, the optical (light) source and detection equipment described hereinafter are located in the tool 10, e.g. in an upper electronics housing 32.

According to the preferred embodiment of the invention, the probes 30 are of compact size, usually just 0.2 to 0.4 mm in diameter (e.g., a diameter of 0.385 mm being shown between arrows in FIGS. 2a, 3a, 4a, and 4b). The small size results in minimal disturbance to the sensing flow and the capability of detecting smaller oil drops or gas bubbles. Probe sizes smaller than 0.2 mm are not preferred because they often result in inadequate signals. The preferred probe material is sapphire because of its superior mechanical strength and suitable index of refraction. In addition, sapphire is generally resistant to abrasive materials found in wellbores. However, sapphire, like certain color glass filters can fluoresce. Since fluorescence of the probe could add to background noise and reduces the signal-to-noise ratio, it is desirable to reduce the fluorescence of the sapphire by annealing the probe in a hydrogen atmosphere at a temperature above 700 C.

Figure 2A:
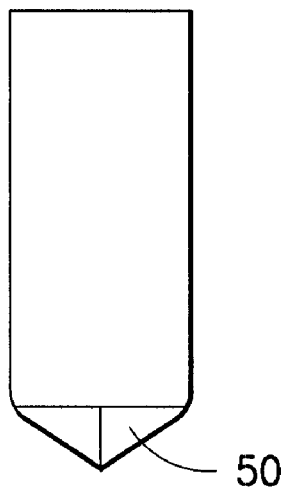
FIG. 2a is a schematic diagram of a probe having a cubical corner tip according to a first embodiment of the invention.
Figure 2B:
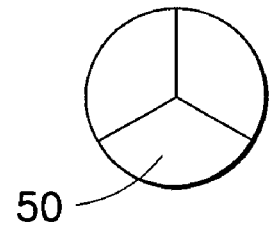
Figure 2C:
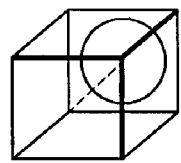
FIG. 2c is a perspective view of a cube which illustrates the manner in which the cubical corner probe tip of FIGS. 2a and 2b is shaped.

Turning now to FIGS. 2a-2c, a first embodiment of a probe according to the invention is particularly designed for sensing the reflectance. The tip 50 of the probe comprises a cubical corner, i.e., three planes perpendicular to each other. Such an optical element has a unique property. Namely, should the three planes be mirrors, then any light beam cast on the inner quadrant of the cubical will be reflected back along the direction from which it comes, regardless of the incident angle.

According to the preferred embodiment of tip 50, the diagonal of the cubical corner (shown dotted in FIG. 2c) aligns with the axis of the probe. Thus, light coming towards the probe tip will be subject to triple partial reflections (once at each surface) and be sent back. For those rays that are parallel to the probe (optical) axis, the incident angle at each of the three planes is the same and will equal 54.73. For purposes of the invention, the tip will be considered a cubical corner if the incident angle at each of the planes is 54.73±1. The provided probe has several advantages over the prior art. First, the returning signal of reflection is fully collected since it follows the same but reversed direction of incidence, and light paths are reversible. Second, because of the triple reflection, the ratio of contrast is enhanced by the power of three (as opposed to the oblique probes of the prior art which were enhanced by the power of two). Third, the dominant portion of the light power resides in the lowest mode of the fiber, i.e., parallel to the probe axis, and therefore has an incident angle of approximately 55. This angle is close to the optimal incidence for sapphire and silica materials alike. In addition, it has been found that the cubical corner tip geometry helps expedite the drainage of residue crude oils.

Figure 2D:
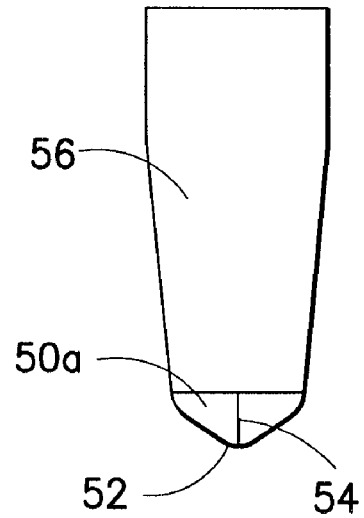
FIG. 2d is a schematic diagram of a modified cubical corner probe tip with a rounded tip and taper.

Turning to FIG. 2d, a probe tip 50a similar to the probe tip 50 of FIGS. 2a-2c is seen. In FIG. 2d, the cubical corner of the probe tip has been rounded off by slightly flattening the corner 52 and the edges 54. In addition, the base 56 adjacent the probe tip has been tapered over a distance of about 0.6 mm by an angle of approximately five degrees relative to the probe axis. The rounding off of the corner facilitates the drainage of fluids and reduces the effect of residue films. The tapering base also facilitates the drainage of fluids by presenting a smaller front end. In addition, the taper also creates certain optical properties that are desirable for fluorescence detection.

Figure 3A:
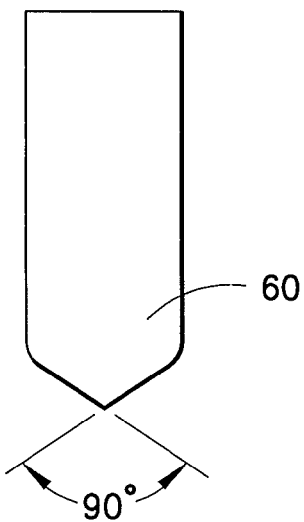
FIG. 3a is a schematic diagram of a conical probe tip according to a second embodiment of the invention.

A second embodiment of a probe tip is seen in FIG. 3a. The probe tip 60 of the second embodiment comprises a 45 cone; i.e., lines on opposite "sides" of the cone are angled at 90 relative to each other, and a line drawn along the conical surface makes a forty-five degree angle relative to the probe axis. With the 45 conical design, light will bounce twice instead of three times, but retain the same orientation on the way back. For purposes of this invention, any cone which is 45±2 will be considered a 45 cone.

Figure 3B:
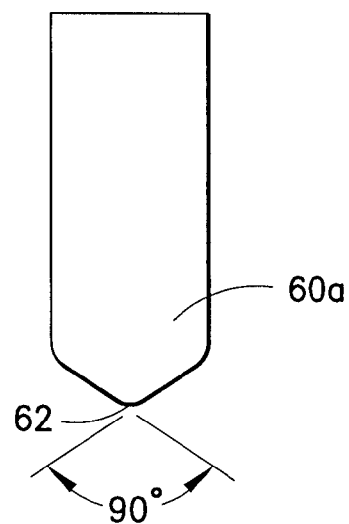
FIG. 3b is a schematic diagram of a modified rounded conical probe tip.

A first modified conical probe tip 60a is seen in FIG. 3b. The probe tip 60a is similar to probe tip 60 of FIG. 3a except that the point 62 is slightly flattened (rounded). Preferably, the area of flattening for both the modified conical probe tip 60a and the modified cubical corner probe tip 50a (FIGS. 3b and 2d) is at most twenty-five percent (and more desirably, at most fifteen percent) of the width of the fiber. In the preferred embodiment, the area of flattening is more preferably at most twenty-five percent (and more desirably, at most fifteen percent) the width of the fiber at the transition location from the taper (if any) to the cone or to the cubical corner).

Figure 3C:
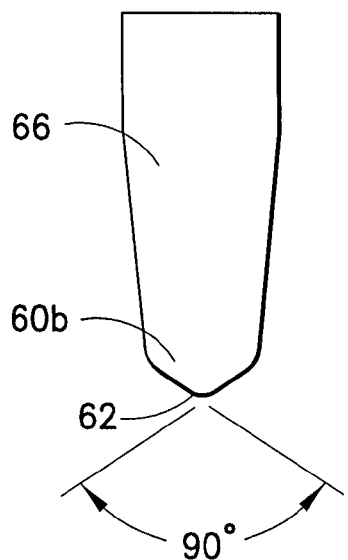
FIG. 3c is a schematic diagram of a modified rounded conical probe with a taper.

Similarly, a second modified conical probe tip 60b is seen in FIG. 3c. The probe tip 60b is similar to probe tip 60 of FIG. 3a except that the base 66 of the probe tip has been tapered down to a diameter of 0.28 mm over a distance of about 0.6 mm by an angle of approximately five degrees relative to the probe axis. It will be appreciated, that if desired, probe tip 60b can also be modified to have point 62 flattened as in the modification of FIG. 3b.

Figure 4A:
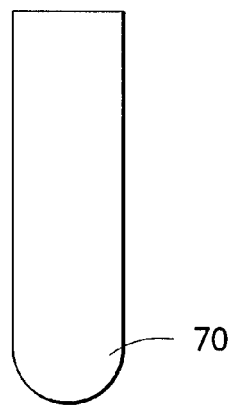
FIG. 4a is a schematic diagram of a spherical probe tip according to a third embodiment of the invention.

A third embodiment of a probe tip which is particularly designed for fluorescence detection is seen in FIG. 4a. The probe tip 70 of the third embodiment is substantially spherical such that the tip 70 comprises a hemisphere. Alternatively, the probe tip 70 may be a paraboloid. As is discussed hereinafter, the probe tip of the third embodiment has a small numeric aperture (i.e., a numeric aperture preferably less than 0.3) and is therefore "far-sighted".

Figure 4B:
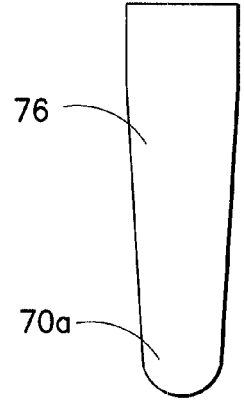
FIG. 4b is a schematic diagram of the probe tip of FIG. 4a with a taper.

A modification to the substantially spherical probe of FIG. 4a is seen in FIG. 4b where base 76 of the probe tip 70a has been tapered down to a diameter of 0.28 mm over a distance of about 1 mm by an angle of approximately three degrees relative to the probe axis.

Figure 5A:
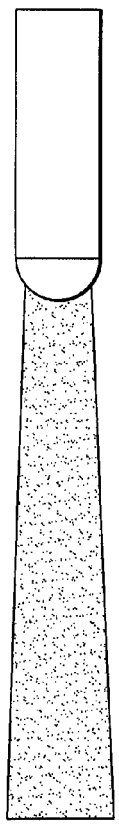
FIG. 5a is a schematic diagram illustrating the narrow aperture and resulting long beam of the spherical probe tip.
Figure 5B:
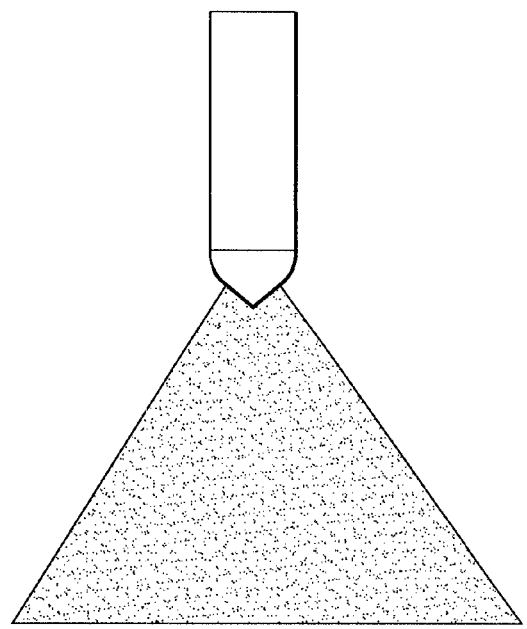
FIG. 5b is a schematic diagram illustrating the relatively larger aperture and resulting shorter broader beam of the conical probe tip.

Which of the previously described probes is optimal for use in a given circumstance depends upon the parameters of the circumstance. In particular, the measurement principles related to reflectance and fluorescence are quite different. For reflectance, the measurement involves an evanescent field that exists at only the boundary of media. Thus, the reflectance measurement is a good indicator of the hold-up of the fluid passing the probe. On the other hand, fluorescence is a bulk measurement, and unlike the circumstances relating to reflectance, the fluorescence detector is able to "see" oil drops before they impact the probe. This ability to see drops moving enables the capability of detecting oil drop velocity. How far a probe "sees" depends significantly on the optical shape of the probe tip. In fact, whether a probe is far-sighted or near-sighted is dictated by the way that the light exits the probe. As seen in FIG. 5a, some probes (such as the spherical or paraboloid probes of FIGS. 4a and 4b) eject a pencil-like beam that reaches a (relatively) long distance from the tip. These probes have a small numerical aperture (NA); preferably between 0.2 and 0.3. On the other hand, as seen in FIG. 5b, other probes such as the probes of FIGS. 2a, 2d, 3a, 3b, and 3c spread the light across in front of the tip forming a large cone. These probes have a large NA; typically greater than 0.8.

Aside from the fluorescent yield of different crude oils, the generation of a signal from a spatial point is in proportion to the square of the light intensity that falls on the point. If signal strength is an important factor (as it is for fluorescence), it is desirable to concentrate the light. The sensing region of large NA probe is disperse and very localized (FIG. 5b); i.e., its vision falls quickly beyond the focal point. In contrast, the decrease of light intensity (due to dispersion and/or attenuation) over the distance is much gradual in the small NA probes (FIG. 5a), giving them an extended vision. That is why small NA probes are "far-sighted", whereas large NA probes are "near-sighted". As a result, the two kinds of probes are particularly suitable for different usages. As suggested above, the small NA probes are particularly suited for velocity measurement, while the large NA probes provide an abrupt response at the crossover of phase boundaries, and are particularly suited for sensing the holdups of the fluid.

The size of the numerical aperture of the probe is a function of the radius r of the tip. This is the result of a principle in geometrical optics, that is, $(NA \times r)^{-1} \leq B$ for any passive transformation, where B is a quantity associated with the brightness of the source input, either real or virtual. For a finite B, NA increases whenever r decreases. As previously mentioned, several designs of the near-sighted (i.e., large NA) probe are depicted in FIGS. 2a, 2d, 3a, 3b, and 3c. Also, as previously mentioned, all near-sighted probes are particularly useful for reflectance measurements which yield three-phase holdup determinations.

The rounding off of the edges of the probes, as seen in FIGS. 2a, 2d, and 3b, facilitates the fluid flow along the surface. In addition, the rounded off tip pushes the bright spot (or the focal point) slightly away from the surface of the probe tip, thus mitigating the oil film effect in the fluorescence detection. The taper on the probes seen in FIGS. 2d and 3c serves dual purposes. The taper effectively sharpens the probe tip, thereby minimizing the residue film thickness, and at the same time increasing the NA of the probe. This change of NA is an effective way of raising signal level while retaining the freedom of choice at the tip geometry. When using a taper, it is preferred that the following condition is satisfied: $(NA_0 \times r) \geq (NA \times R)$, where NA and R are the numerical aperture of the incident light and the radius of the taper at the large end, respectively. While r is the radius at the small end, $NA_0$ denotes NA of the probe at that end. If the condition is violated, light may leak through the side of the taper into the surrounding fluid. This will result in a decrease of the signal level and undesired responses. It should be pointed out that adding the taper alters the angle of incident light but does not degrade the probe performance for reflectance, because both the cubical corner and the forty-five degree cone embodiments of FIGS. 2 and 3 preserve the orientation of light.

As previously suggested, the spherical tip of the embodiment of FIG. 4a functions as a lens which collimates exiting light into a narrow beam, while at the same time draining fluids off the tip. The curvature of the tip may vary with needs according to the indices of refraction of both the probe and the crude oil. A parabolic curve is one of such alternatives. In addition, adding a minor taper (as seen in FIG. 4b) helps to minimize the lingering time of fluids around the tip or the oil film effect, improving the promptness of the probe recovery. At the same time it should be noted that the taper increases the NA, and too large a taper could undermine the far-sighted property of the spherical or paraboloidal tip.

If a single probe is to serve dual purposes of measuring reflectance and fluorescence (for holdup and velocity respectively), a compromised design can be attained. For instance, changing the cone tip of FIGS. 3a-3c into a partial sphere (i.e., rounding off the tip substantially) would extends the distance of the probe vision. The larger the extent of the replacement, the farther the sensing distance. When a hemisphere replaces the entire cone, the near-sighted probe evolves into a far-sighted. In the other direction, one may substitute the hemisphere with a parabolic tip to shorten the probe vision. Another approach to a dual-purpose probe is incorporating a substantial taper (5 to 10 degrees) to a spherical lens tip, such that the tip diameter is reduced to one-third to two-thirds of its original size. All these combinations allow realization of any NA value between the two extremes. The best form would depend on flow conditions such as the type of crude oil, drop/bubble size and the velocity of the flow.

Alternatively, rather than using compromised design for a dual-purpose probe, in accord with one preferred aspect of the invention, two probes of optimized design may be used in conjunction with each other; a first far-sighted probe optimized for fluorescence detection, and a second near-sighted probe optimized for reflectance detection.

There have been described and illustrated herein several embodiments of a optical probes. While particular embodiments of the invention have been described, it is not intended that the invention be limited thereto, as it is intended that the invention be as broad in scope as the art will allow and that the specification be read likewise. Thus, while the invention was described with reference to a particular wellbore tool, it will be appreciated that stationary apparatus and/or plumbing can be utilized in or around the wellbore and may be cemented into place, or other wellbore tools could be utilized. Also, while the invention was described with reference to particular probe materials (e.g., sapphire and silica), particular fiber sizes, and particular angles, it will be appreciated that other materials, sizes, and angles can be utilized within the scope of the invention. It will therefore be appreciated by those skilled in the art that yet other modifications could be made to the provided invention without deviating from its spirit and scope as claimed.

We claim:

1. An optical apparatus for investigating a hydrocarbon-containing fluid stream in a hydrocarbon wellbore, comprising:

an optical probe operably coupled to a light source for supplying light excitation to said optical probe and a light detection means for detecting light collected by said optical probe, wherein said optical probe comprises a continuous optical fiber disposed in the hydrocarbon-containing fluid stream, said continuous optical fiber having a first portion of substantially constant diameter and a tip formed as a substantially uniform cone having a conical face angled at 45°±2° relative to a longitudinal axis, said substantially uniform cone extending to said first portion and having a diameter where said tip joins said first portion equal to said substantially constant diameter.

2. An optical apparatus according to claim 1, wherein: said tip terminates at a sharp point.

3. An optical apparatus according to claim 1, wherein: said tip terminates at a symmetrically rounded tip portion, said rounded tip having a diameter at most twenty-five percent of a width of said optical probe at a base adjacent said cone.

4. An optical apparatus according to claim 1, wherein: said substantially constant diameter is between 0.2 mm and 0.4 mm.

5. An optical apparatus for investigating a hydrocarbon-containing fluid stream in a hydrocarbon wellbore, comprising:

an optical probe operably coupled to a light source for supplying light excitation to said optical probe and a light detection means for detecting light collected by said optical probe, wherein said optical probe comprises a continuous optical fiber disposed in the hydrocarbon-containing fluid stream, said continuous optical fiber having a first portion of substantially constant diameter, a tapering portion connected to said first portion, and a tip connected to said tapering portion, said tip formed as a substantially uniform cone having a conical face angled at 45°±2° relative to a longitudinal axis, said tapering portion having a first diameter equal to said substantially constant diameter of said first portion where said tapering portion is connected to said first portion and having a second diameter smaller than said substantially constant diameter where said tip is connected to said tapering portion, said cone having a diameter equal to said second diameter where said cone is connected to said tapering portion.

6. An optical apparatus according to claim 5, wherein: said tapering portion has a taper is less than 10°.

7. An optical apparatus according to claim 5, wherein: said tapering portion has a taper is at most 5°.

8. An optical apparatus for investigating a fluid stream flowing in a well, comprising:
   a) a tool having an elongate body having a longitudinal axis and suspended in the well;
   b) a light source; and
   c) a plurality of optical probes coupled to said elongate body and to said light source, said plurality of optical probes including at least one probe comprising an optical fiber having a distal end arranged as a substantially cubical corner defined by three planes substantially perpendicular to each other and not parallel to a plane including said longitudinal axis.

9. A method for investigating a hydrocarbon-containing fluid stream in a hydrocarbon wellbore, comprising:

suspending a tool in the wellbore, the tool including at least one optical probe operably coupled to a light source and light detection means, wherein said optical probe comprises a continuous optical fiber disposed in the hydrocarbon-containing fluid stream, said continuous optical fiber having a first portion of substantially constant diameter and a tip formed as a substantially uniform cone having a conical face angled at 45°±2° relative to a longitudinal axis, said substantially uniform cone extending to said first portion and having a diameter where said tip joins said first portion equal to said substantially constant diameter; and operating said light source to supply light excitation to said optical probe and operating said light detection means to detect light collected by said optical probe in order to investigate the hydrocarbon-containing fluid stream in the wellbore.

10. A method for investigating a hydrocarbon-containing fluid stream in a hydrocarbon wellbore, comprising:

suspending a tool in the wellbore, the tool including at least one optical probe operably coupled to a light source and light detection means, wherein said optical probe comprises a continuous optical fiber disposed in the hydrocarbon-containing fluid stream, said continuous optical fiber having a first portion of substantially constant diameter, a tapering portion connected to said first portion, and a tip connected to said tapering portion, said tip formed as a substantially uniform cone having a conical face angled at 45°±2° relative to a longitudinal axis, said tapering portion having a first diameter equal to said substantially constant diameter of said first portion where said tapering portion is connected to said first portion and having a second diameter smaller than said substantially constant diameter where said tip is connected to said tapering portion, said cone having a diameter equal to said second diameter where said cone is connected to said tapering portion; and operating said light source to supply light excitation to said optical probe and operating said light detection means to detect light collected by said optical probe in order to investigate the hydrocarbon-containing fluid stream in the wellbore.

* * * * *